(12) United States Patent
Kim et al.

(10) Patent No.: US 12,009,071 B2
(45) Date of Patent: Jun. 11, 2024

(54) SYSTEM AND/OR METHOD FOR DETERMINING SERVICE CODES FROM ELECTRONIC SIGNALS AND/OR STATES USING MACHINE LEARNING

(71) Applicant: AKASA, Inc., South San Francisco, CA (US)

(72) Inventors: Byung-Hak Kim, San Jose, CA (US); Hariraam Varun Ganapathi, San Francisco, CA (US)

(73) Assignee: AKASA, INC., South San Francisco, CA (US)

( * ) Notice: Subject to any disclaimer, the term of this patent is extended or adjusted under 35 U.S.C. 154(b) by 466 days.

(21) Appl. No.: 17/206,021

(22) Filed: Mar. 18, 2021

(65) Prior Publication Data

US 2022/0165373 A1   May 26, 2022

Related U.S. Application Data

(60) Provisional application No. 63/116,764, filed on Nov. 20, 2020.

(51) Int. Cl.
*G16H 10/60* (2018.01)
*G06F 40/216* (2020.01)
*G06F 40/284* (2020.01)
*G06F 40/30* (2020.01)
*G06N 3/045* (2023.01)
*G06N 3/08* (2023.01)

(52) U.S. Cl.
CPC .......... *G16H 10/60* (2018.01); *G06F 40/284* (2020.01); *G06N 3/045* (2023.01); *G06N 3/08* (2013.01)

(58) Field of Classification Search
CPC ...... G16H 10/60; G06H 50/70; G06F 40/284; G06F 40/28; G06F 40/30; G06F 40/216; G06F 40/295; G06F 40/169; G06F 16/951; G06F 16/9535; G06F 16/3344; G06F 16/24578; G06F 16/313; G06F 16/345; G06F 16/93; G06F 17/2785; G06F 17/278; G06F 9/50; G06F 21/6245; G06F 21/624; G06N 3/045; G06N 3/08; G06N 20/00
USPC .......................................................... 704/1–9
See application file for complete search history.

(56) References Cited

U.S. PATENT DOCUMENTS

| | | | |
|---|---|---|---|
| 2016/0048655 A1* | 2/2016 | Maitra .................. | G16H 70/40 705/3 |
| 2020/0279105 A1* | 9/2020 | Muffat .................... | G06N 3/08 |
| 2020/0402625 A1* | 12/2020 | Aravamudan ...... | G06F 21/6245 |

OTHER PUBLICATIONS

Label Studio, Open Source, "Data Labeling Platform," https://labelstud.io/, Nov. 8, 2023, 6 pages.
Crawford, "Truth about Computer-Assisted Coding: A Consultant, HIM Professional, and Vendor Weigh in on the Real CAC Impact," Journal of AHIMA 84, No. 7 (Jul. 2013): 24-27, 5 pages.

(Continued)

*Primary Examiner* — Leshui Zhang
(74) *Attorney, Agent, or Firm* — Berkeley Law & Technology Group, LLP

(57) ABSTRACT

Disclosed are a system, method and apparatus to generate service codes based, at least in part, on electronic documents. In an embodiment, tokens may be embedded in an electronic document based, at least in part, on a linguistic analysis of the electronic document. Likelihoods of applicability of service codes to the electronic document may be determined based, at least in part, on the embedding of tokens.

19 Claims, 5 Drawing Sheets

(56) References Cited

OTHER PUBLICATIONS

Hinton, et al, "Distilling the Knowledge in a Neural Network," NeurIPS 2014 Deep Learning and Representation Learning Workshop, 2014, arXiv:1503.02531v1 [stat.ML] Mar. 19, 2015, 9 pages.
Makhzani, et al, "Adversarial Autoencoders," arXiv:1511.05644v2 [cs.LG], May 25, 2016, 16 pages.
Ba, et al, "Layer Normalization," arXiv:1607.06450v1 [stat.ML], Jul. 21, 2016, 14 pages.
Vaswani, et al, "Attention Is All You Need," 31st Conference on Neural Information Processing Systems (NIPS 2017), arXiv:1706.03762v5 [cs.CL], Dec. 6, 2017, 15 pages.
Lin, et al, "Focal Loss for Dense Object Detection," Proceedings of International Conference on Computer Vision (ICCV 2017), 2017, arXiv:1708.02002v2 [cs.CV], Feb. 7, 2018, 10 pages.
Baumel, et al, "Multi-Label Classification of Patient Notes: Case Study on ICD Code Assignment," arXiv:1709.09587v3 [cs.CL], Nov. 20, 2017, 8 pages.
Shi, et al, "Towards Automated ICD Coding Using Deep Learning," arXiv:1711.04075v3 [cs.CL], Nov. 30, 2017, 11 pages.
Huang, et al, "An Empirical Evaluation of Deep Learning for ICD-9 Code Assignment using MIMIC-III Clinical Notes," arXiv:1802.02311v2 [cs.CL], Jun. 8, 2019, 22 pages.
Mullenbach, et al, "Explainable Prediction of Medical Codes from Clinical Text," arXiv:1802.05695v2 [cs.CL], Apr. 16, 2018, 11 pages.
Izmailov, et al, "Averaging Weights Leads toWider Optima and Better Generalization," arXiv:1803.05407v3 [cs.LG], Feb. 25, 2019, 12 pages.
Hjelm, et al, "Learning Deep Representations by Mutual In-Formation Estimation and Maximization," arXiv:1808.06670v5 [stat.ML], Feb. 22, 2019, 24 pages.
Velickovic, et al, "Deep Graph Infomax," arXiv:1809.10341v2 [stat.ML], Dec. 21, 2018, 17 pages.
Lee, et al, "BioBERT: a pre-trained biomedical language representation model for biomedical text mining," Bioinformatics, 2019, 1-7, doi: 10.1093/bioinformatics/btz682, Advance Access Publication Date: Sep. 10, 2019, 7 pages.
Alsentzer, et al, "Publicly Available Clinical BERT Embeddings," arXiv:1904.03323v3 [cs.CL], Jun. 20, 2019, 7 pages.
Peng, et al, "Transfer Learning in Biomedical Natural Language Processing: An Evaluation of BERT and ELMo on Ten Benchmarking Datasets," arXiv:1906.05474v2 [cs.CL], Jun. 18, 2019, 8 pages.
Yu, "ICD Coding from Clinical Text Using Multi-Filter Residual Convolutional Neural Network," arXiv:1912.00862v1 [cs.CL], Nov. 25, 2019, 9 pages.
Nuthakki, et al, "Natural language processing of MIMIC-III clinical notes for identifying diagnosis and procedures with neural networks," ResearchGate, https://www.researchgate.net/publication/338292165, Dec. 2019, 11 pages.
Vu, et al, "A Label Attention Model for ICD Coding from Clinical Text," arXiv:2007.06351v1 [cs.CL], Jul. 13, 2020, 7 pages.
Gu, et al, "Domain-Specific Language Model Pretraining for Biomedical Natural Language Processing," vol. 1, No. 1, Article 1. Publication date: Jan. 2021, arXiv:2007.15779v6 [cs.CL], Sep. 16, 2021, 24 pages.
Ji, et al, "Dilated Convolutional Attention Network for Medical Code Assignment from Clinical Text," In Proceedings of the 3rd Clinical Natural Language Processing Workshop, pp. 73-78, Online. Association for Computational Linguistics, arXiv:2009.14578v1 [cs.CL], Sep. 30, 2020, 6 pages.
Zhang, et al, "BERT-XML: Large Scale Automated ICD Coding Using BERT Pretraining," Proceedings of the 3rd Clinical Natural Language Processing Workshop, Nov. 19, 2020, 11 pages.
Liu, et al, "Effective Convolutional Attention Network for Multilabel Clinical Document Classification," Proceedings of the 2021 Conference on Empirical Methods in Natural Language Processing, Nov. 7-11, 2021, pp. 5941-5953.
Deng, et al, "HTCInfoMax: A Global Model for Hierarchical Text Classification via Information Maximization," Proceedings of the 2021 Conference of the North American Chapter of the Association for Computational Linguistics: Human Language Technologies, Jun. 6-11, 2021, pp. 3259-3265.
Kim, et al, "Read, Attend, and Code: Pushing the Limits of Medical Codes Prediction from Clinical Notes by Machines," In Proceedings of the 6th Machine Learning for Healthcare Conference (MLHC 2021), vol. 149 of Proceedings of Machine Learning Research, arXiv:2107.10650v1 [cs.CL], Jul. 10, 2021, 12 pages.
Sun, et al, "Multi-task Balanced and Recalibrated Network for Medical Code Prediction," In European Conference on Machine Learning and Principles and Practice of Knowledge Discovery in Databases (ECML PKDD 2021), arXiv:2109.02418v1 [cs.CL], Sep. 6, 2021, 10 pages.
Yuan, et al, "Code Synonyms Do Matter: Multiple Synonyms Matching Network for Automatic ICD Coding," In Proceedings of the 60th Annual Meeting of the Association for Computational Linguistics (ACL 2022), arXiv:2203.01515v2 [cs.CL], Mar. 31, 2022, 7 pages.
Leng, et al, "Polyloss: a Polynomial Expansion Perspective of Classification Loss Functions," In 10th International Conference on Learning Representations (ICLR 2022), arXiv:2204.12511v2 [cs.CV], May 10, 2022, 16 pages.
Wikipedia, "Activation function," https://en.wikipedia.org/w/index.php?title=Activation_function&oldid=1006898538, last edited on Feb. 15, 2021, 5 pages.
Wikipedia, "Backpropagation," https://en.wikipedia.org/w/index.php?title=Backpropagation&oldid=1004996874, last edited on Feb. 5, 2021, 8 pages.
Wikipedia, "Convolutional neural network," https://en.wikipedia.org/w/index.php?title=Convolutional_neural_network&oldid=1006600870, last edited on Feb. 13, 2021, 30 pages.
Budhiraja, "Dropout in (Deep) Machine learning," https://medium.com/@amarbudhiraja/https-medium-com-amarbudhiraja-learning-less-to-learn-better-dropout-in-deep-machine-learning-74334da4bfc5, Feb. 17, 2021, 6 pages.
Wikipedia, "Ensemble learning," https://en.wikipedia.org/w/index.php?title=Ensemble_learning&oldid=998897741, last edited on Jan. 7, 2021, 13 pages.
Bell, et al, "Epoch (machine learning)," Epoch (machine learning) | Radiology Reference Article | Radiopaedia.org, https://radiopaedia.org/articles/epoch-machine-learning?lang=us#:~:text=An epoch is a term,of data is very large, Feb. 17, 2021, 6 pages.
Keras, "GlobalMaxPooling1D layer," GlobalMaxPooling1D layer, https://keras.io/api/layers/pooling_layers/global_max_pooling1d/, Feb. 17, 2021, 1 page.
Rehurek, et al, "Software Framework for Topic Modelling with Large Corpora," In Proceedings of the LREC 2010 Workshop on New Challenges for NLP Frameworks, Valletta, Malta. ELRA, May 22, 2010, 5 pages.
Luong, et al, "Effective Approaches to Attention-based Neural Machine Translation," arXiv:1508.04025v5 [cs.CL], Sep. 20, 2015, 11 pages.
Koehrsen, "Overfitting vs. Underfitting: A CompleteExample," Overfitting vs. Underfitting: A Complete Example | by Will Koehrsen | Towards Data Science, https://towardsdatascience.com/overfitting-vs-underfitting-a-complete-example-d05dd7e19765, Jan. 28, 2018, 12 pages.
Kaji, et al, "An attention based deep learning model of clinical events in the intensive care unit," https://doi.org/10.1371/journal.pone.0211057, Feb. 13, 2019, 17 pages.
Johnson, et al, "Data Descriptor: MIMIC-III, a freely accessible critical care database," www.nature.com/scientificdata, Scientific Data | 3:160035 | DOI: 10.1038/sdata.2016.35, May 24, 2016, 9 pages.
Li, et al, "Automated ICD-9 Coding via a Deep Learning Approach," IEEE/ACM Transactions on Computational Biology and Bioinformatics, vol. 16, No. 4, Jul./Aug. 2019, 10 pages.
Alammar, "The Illustrated Transformer," The Illustrated Transformer—Jay Alammar—Visualizing machine learning one concept at a time, https://jalammar.github.io/illustrated-transformer/, Feb. 17, 2021, 23 pages.

(56) References Cited

OTHER PUBLICATIONS

Shrank, et al, "Waste in the US Health Care System Estimated Costs and Potential for Savings," JAMA | Special Communication, Clinical Review & Education, JAMA. doi:10.1001/jama.2019.13978, Oct. 7, 2019, 9 pages.

Gensim, "Word2Vec Model," https://radimrehurek.com/gensim/auto_examples/tutorials/run_word2vec.html, last updated Dec. 21, 2022, 22 pages.

Wikipedia, "Word2vec," https://en.wikipedia.org/w/index.php?title=Word2vec&oldid=1006343323, last edited on Feb. 12, 2021, 6 pages.

Li, "ICD Coding from Clinical Text Using Multi-Filter Residual Convolutional Neural Network," In Proceedings of the Thirty-Fourth AAAI Conference on Artificial Intelligence (AAAI 2020), arXiv:1912.00862v1 [cs.CL], Nov. 25, 2019, 9 pages.

Chen, et al, "A Multi-channel Convolutional Neural Network for ICD Coding," IEEE 978-1-7281-2348-6/19, 2019, downloaded Nov. 9, 2023, 7 pages.

Xie, et al, "EHR Coding with Multi-scale Feature Attention and Structured Knowledge Graph Propagation," Session Long-Knowledge Graph I, CIKM, Nov. 3-7, 2019, 10 pages.

GitHub, HumanSignal/label-studio, "Label Studio is a multi-type data labeling and annotation tool with standardized output format," https://github.com/HumanSignal/label-studio, downloaded Nov. 9, 2023, 8 pages.

CDC, Centers for Disease Control and Prevention, National Center for Health Statistics, "Classification of Diseases, Functioning, and Disability," Last reviewed Jul. 23, 2021, 1 page.

\* cited by examiner

SYSTEM AND/OR METHOD FOR DETERMINING SERVICE CODES FROM ELECTRONIC SIGNALS AND/OR STATES USING MACHINE LEARNING

This application claims the benefit of priority to U.S. Provisional Patent Application No. 63/116,764 titled "SYSTEM AND/OR METHOD FOR DETERMINING SERVICE CODES FROM ELECTRONIC SIGNALS AND/OR STATES", filed on Nov. 20, 2020, assigned to the assignee of claimed subject matter, and incorporated herein by reference in its entirety.

BACKGROUND

1. Field

This disclosure relates to methods and/or techniques for determining service codes based, at least in part, on expressions in electronic documents.

2. Information

Modern services, such as clinical medical services, are typically funded through insurance and/or reimbursement plans. In an implementation, specific types of services may be classified and identified by corresponding service codes. Parties that are to make payment to settle fees for a service provided may then make an amount of payment to a service provider based on service code(s) associated with the service. In the particular example of clinical medical service codes, the continued growth in volume and complexity of clinical service codes is increasingly burdening medical service providers seeking payment for services.

BRIEF DESCRIPTION OF DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1:
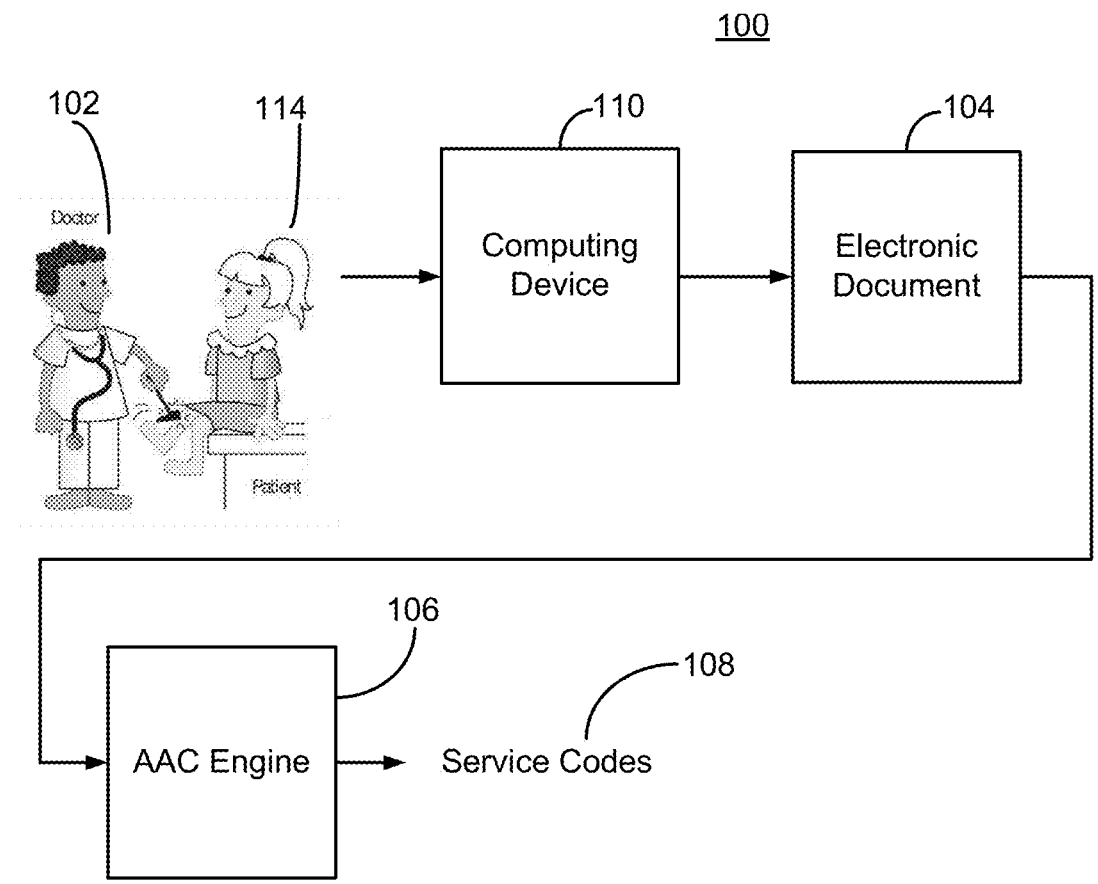
FIG. 1 is a schematic diagram of a system to generate codes relating to services according to an embodiment.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Furthermore, structural and/or other changes may be made without departing from claimed subject matter. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents. Further, it is to be understood that other embodiments may be utilized. Also, embodiments have been provided of claimed subject matter and it is noted that, as such, those illustrative embodiments are inventive and/or unconventional; however, claimed subject matter is not limited to embodiments provided primarily for illustrative purposes. Thus, while advantages have been described in connection with illustrative embodiments, claimed subject matter is inventive and/or unconventional for additional reasons not expressly mentioned in connection with those embodiments. In addition, references throughout this specification to "claimed subject matter" refer to subject matter intended to be covered by one or more claims, and are not necessarily intended to refer to a complete claim set, to a particular combination of claim sets (e.g., method claims, apparatus claims, etc.), or to a particular claim.

DETAILED DESCRIPTION

References throughout this specification to one implementation, an implementation, one embodiment, an embodiment, and/or the like means that a particular feature, structure, characteristic, and/or the like described in relation to a particular implementation and/or embodiment is included in at least one implementation and/or embodiment of claimed subject matter. Thus, appearances of such phrases, for example, in various places throughout this specification are not necessarily intended to refer to the same implementation and/or embodiment or to any one particular implementation and/or embodiment. Furthermore, it is to be understood that particular features, structures, characteristics, and/or the like described are capable of being combined in various ways in one or more implementations and/or embodiments and, therefore, are within intended claim scope. In general, of course, as has always been the case for the specification of a patent application, these and other issues have a potential to vary in a particular context of usage. In other words, throughout the patent application, particular context of description and/or usage provides helpful guidance regarding reasonable inferences to be drawn; however, likewise, "in this context" in general without further qualification refers to the context of the present patent application.

To address burdens in associating services to service codes in billing operations, clinical medicine service providers may employ automated clinical coding (ACC) that uses natural language processing (NLP) to automatically generate diagnosis and procedure medical codes from clinical notes. In an example implementation, computer-assisted coding (CAC) software may scan medical documentation in electronic health records (EHR) to identify essential information and suggest codes for a particular treatment or service. A human coder or health care provider may review codes produced by CAC. In an embodiment, CAC may reduce an administrative burden on service providers, allowing service providers to increasingly focus on delivering care rather than learning the nuances of coding.

As many healthcare facilities have adopted EHRs and clinicians have become more specific in their documentation efforts, coders have had more content to read/process, slowing down a process of associating codes to records. This occurs while there is a growing pressure to expedite claims to insurance companies to receive quick payment. As such, CAC may streamline coding and eliminate bottlenecks while enabling coders to focus more attention on higher-level audits by reviewing service codes that are generated. Notwithstanding improvements in CAC techniques, CAC techniques may be unable to handle increasingly complex medical notes.

According to an embodiment, a linguistic transformation may be trained to determine an embedding of tokens in an electronic document based, at least in part, on a linguistic analysis of the electronic document. Likelihoods of applicability of service codes to the electronic document may then be determined based, at least in part, on the embedding of tokens. In one implementation, a linguistic transformation may be trained using jargon, abbreviations, syntax, grammar and/or of text in a particular service domain such as a medical clinical service domain. It should be understood, however, that this is merely an example of a particular service domain, and that features of the present disclosure may be applied to different service domains without deviating from claimed subject matter. In another implementation, likelihoods of applicability of particular service codes may be determined based, at least in part, on application of one or more attention models to context values associated with individual tokens (e.g., expressed as an "embedding" of tokens). As described below, particular implementations may be scalable to accommodate sets of service codes of different sizes.

FIG. 1 is a schematic diagram of a system 100 to generate service codes relating to medical services according to an embodiment. While particular features of system 100 may be specifically directed to generation of service codes relating to medical services, it should be understood that aspects may be applied for the generation of service codes descriptive of other, different types of services (e.g., other services for which payment/reimbursement is to be pursued from an insurance company). Here, care provider 102 (e.g., physician, physician assistant, registered nurse, etc.) may be evaluating/tending to patient 114 to, for example, provide a diagnosis and/or treatment. In the course of evaluating/tending to patient 114, care provider 102 may record diagnoses and/or treatments in a patient "chart." Such a chart may include, for example, notes that are handwritten, typed and/or spoken to be captured by computing device 110. In a particular implementation, computing device 110 may comprise input devices (not shown) such as, for example, a keyboard, microphone and/or scanning device to receive such notes. Notes received at such an input device may then be processed by computer-readable instructions executed by a processor (e.g., to perform speech to text, character recognition, handwriting recognition and/or spell checking) to generate electronic document 104 expressed as signals and/or states in one or more physical memory devices. In a particular implementation, electronic document 104 may store signals and/or states expressing formatted text to represent notes provided by care provider 102, for example.

AAC engine 106 may comprise one or more computing devices (not shown) to determine service codes 108 based, at least in part, on electronic document 104. AAC engine 106 may comprise, for example, one or more processors and/or processor executable instructions (not shown) to determine service codes 108 based, at least in part, on electronic document 104 using natural language processing. In an embodiment, codes 108 may be reviewed, adjusted and/or corrected by care provider 102 and/or other human auditor before submitting service codes 108 to another entity for billing, payment and/or reimbursement.

Figure 2A:
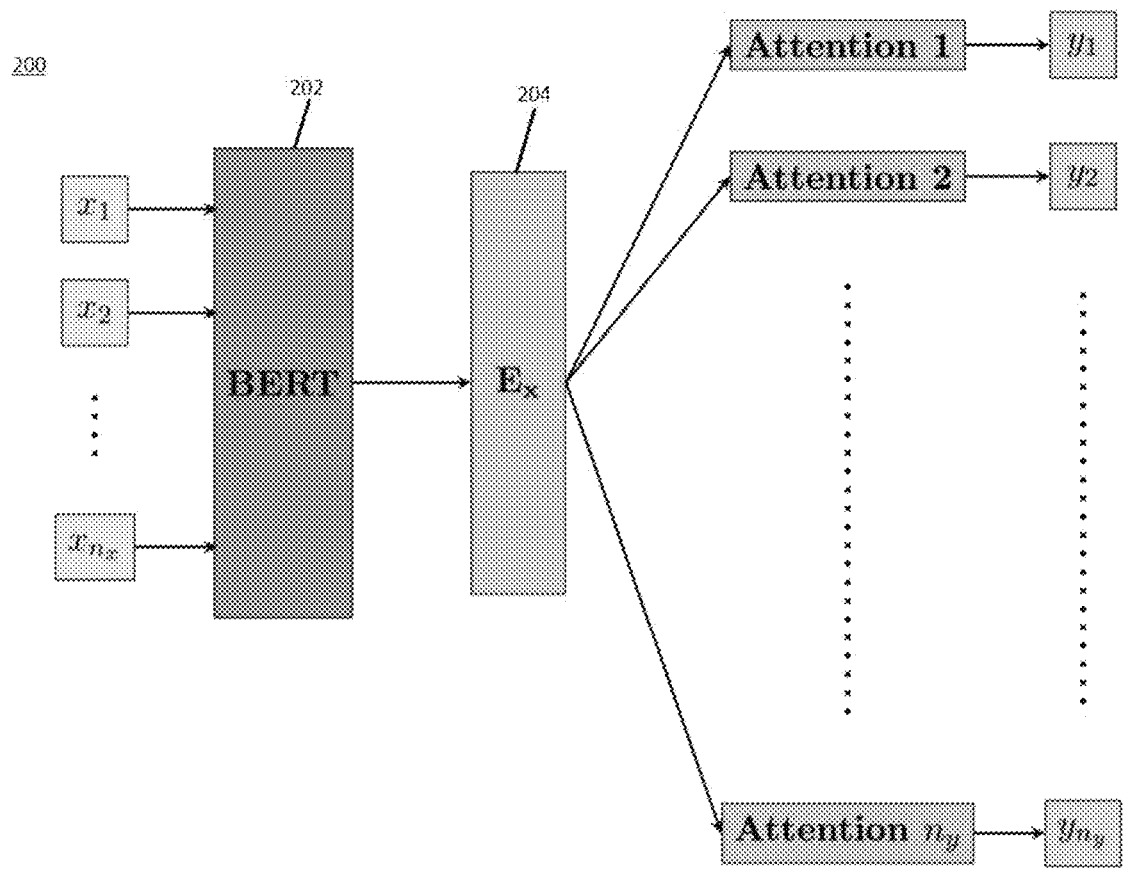
FIG. 2A is a schematic diagram of a system to perform computer-assisted coding (CAC) according to an embodiment.

FIG. 2A is a schematic diagram of a system 200 to perform computer-assisted coding (CAC) according to an embodiment. System 200 may implement features of AAC engine 106 to determine service codes 108, for example. In the particular illustrated implementation, an electronic document may be represented by tokens $x_1$ through $x_{n_x}$ according to a vocabulary of tokens 1 through $n_x$. Here, tokens $x_1$ through $x_{n_x}$ may be generated by a tokenization process. In an example implementation, such tokenization may comprise partitioning/parsing sentences expressed in an electronic document into elements of the sentences such as phrases, words, word fragments and/or punctuation, just to provide a few examples of how a sentence may be partitioned/parsed into discrete elements to represent tokens. In one example embodiment, a vocabulary of tokens may comprise an $n_x$ number of tokens and a token $x_i$ may indicate a presence of a corresponding token i in the vocabulary of tokens (e.g., as a "1" or "0"). Alternatively, a token $x_i$ may indicate and/or map to a likelihood of a presence of a corresponding token i in the vocabulary of tokens (e.g., as a real number between 0.0 and 1.0). In a particular implementation, tokens in a vocabulary of tokens may be specifically tailored and/or weighted according to particular words and/or phrases that are indicative and/or descriptive of clinical medical diagnoses and/or services. In other implementations, tokens in a vocabulary of tokens may be specifically tailored and/or weighted according to particular words and/or phrases that are indicative and/or descriptive of other types of services. Examples of tokens in a vocabulary of tokens specifically tailored and/or weighted according to clinical medical diagnosis/service may comprise, for example, "pain," "fracture" or "fibula", just to provide a few examples.

According to an embodiment, transformer 202 may transform tokens $x_1$ through $x_{n_x}$ to provide an embedding of tokens 204. In a particular implementation, transformer 202 may determine such an embedding of tokens in an electronic document based, at least in part, on a linguistic context of at least some of the associated tokens. For example, transformer 202 may determine such a linguistic context of at least some of associated tokens based, at least in part, on application of a bidirectional encoder representations from transformers (BERT), for example.

In a particular implementation, a BERT implemented in transformer 202 may be trained in a linguistic domain specific using jargon, abbreviations, syntax, grammar and/or text in a medical clinical service domain. While some implementations of a BERT may be limited to use of 512 tokens, a BERT for determining an embedding of tokens may be scalable to determine embeddings of a larger number of tokens to address linguistic features of particular service domains (e.g., medical notes).

According to an embodiment, embedding of tokens 204 may be expressed as an array $E_x$ (e.g., a matrix) populated with context values. For example, $E_x$ may comprise an $n_x \times n_y$ matrix comprising $n_x$ rows corresponding with $n_x$ tokens in a vocabulary of $n_x$ tokens, where context values in a particular row are applicable to corresponding service codes, for example. In an example implementation, context values in a row of $E_x$ may map to corresponding service codes where a context value $E_x(i,j)$ maps a token i to a service code j. According to an embodiment, an attention model may be applied to context values to determine likelihoods of applicability of service codes, for example. In a particular implementation, a likelihood of applicability $y_1$ of a service code i may be computed according to expression (1) as follows:

$$y_1 = \sigma(w_i^T(E_x \alpha_i^T) + b_i), \tag{1}$$

where:

σ is a sigmoid function mapping to a range of real numbers from 0.0 to 1.0;

$\alpha_i$ is a vector of attention coefficients applicable to context values of $E_x$ associated with service code i;

$w_i$ is a vector of weights; and $b_i$ is a bias value.

According to an embodiment, values for $w_i$ and $b_i$ may computed according to a cost function over multiple training epochs and/or training samples. For example, values for $w_i$ and $b_i$ may computed according to a least squares error and/or multi-variable linear regression model, for example. Alternatively, values for $w_i$ and $b_i$ may computed using a neural network optimization model. According to an embodiment, values for $\alpha_i$ may be selected and/or determined to apply an attention model to context values of elements in $E_x$. As may be observed from expression (1), such application of an attention model may comprise computing a dot product of an array of attention coefficients in $\alpha_i$ and an array of at least some of the context values associated with the individual tokens in $E_x$.

According to an embodiment, values for $\alpha_i$ may be determined based, at least in part, on a perceived "alignment" between and/or among tokens in a vocabulary of tokens i through $n_x$. For example, one or more neural networks may be trained to learn such an alignment between and/or among such tokens in the context of accurately mapping to a likelihood of applicability of a particular associated service code. In one particular implementation, such an alignment of tokens may consider a totality of tokens in a vocabulary of tokens according to a "global" attention model. In another particular implementation, such an alignment of tokens may consider a subset of tokens in a vocabulary of tokens according to a "local" attention model.

Figure 2B:
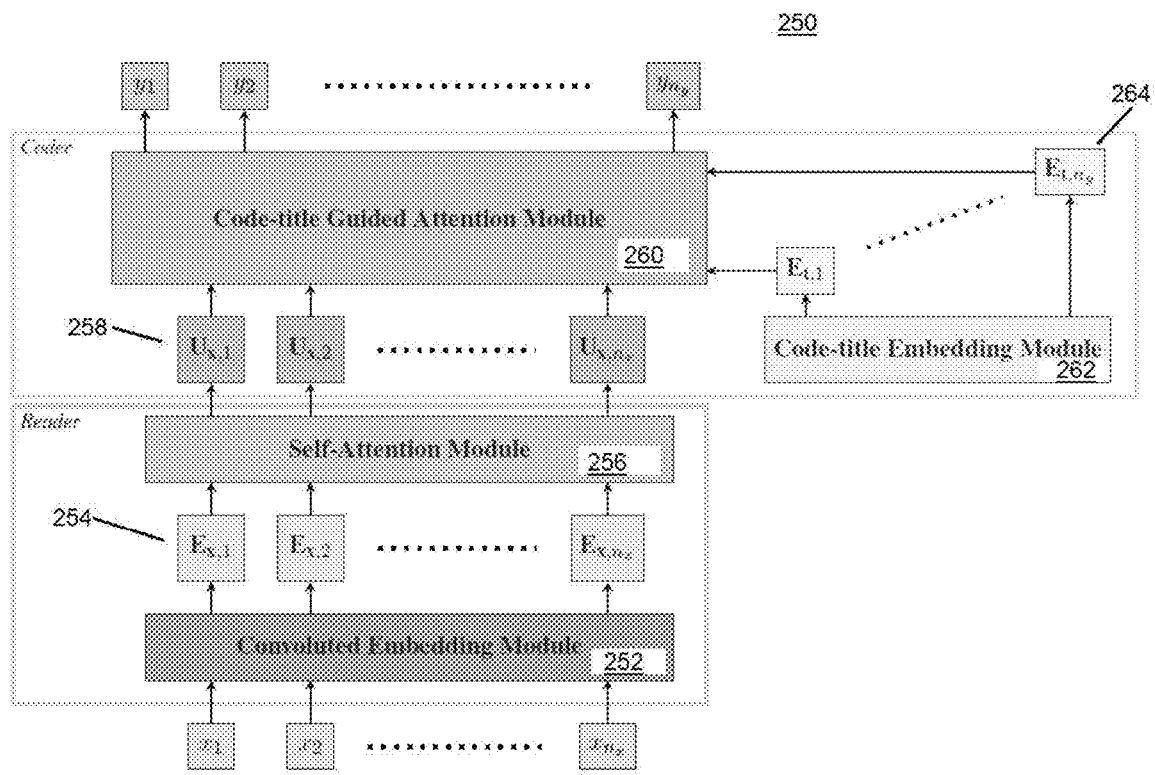
FIG. 2B is a schematic diagram of a system to perform computer-assisted coding (CAC) according to an alternative embodiment.

FIG. 2B is a schematic diagram of a system 250 to perform CAC coding according to an alternative embodiment. Like system 200, system 250 may implement features of AAC engine 106 to determine service codes 108, for example. In a particular implementation, likelihoods of applicability $y_1$ through $y_{n_y}$ of codes 1 through $n_y$ may be determined from tokens $x_1$ through $x_{n_x}$ (from a vocabulary of tokens 1 through $n_x$) based, at least in part, on a processing of tokens $x_1$ through $x_{n_x}$ by a reader to produce an embedding of tokens based, at least in part, on a linguistic context. Such an embedding of tokens may be encoded to provide likelihoods of applicability $y_1$ through $y_{n_y}$. In a particular implementation, over a course of processing text/notes expressed as tokens $x_1$ through $x_{n_x}$ to provide likelihoods of applicability $y_1$ through $y_{n_y}$, relationships between and/or among features of clinical notes in the form of text (e.g., expressed as tokens) and less-frequently applied codes may be learned. Here, a code-title embedding 262 may incorporate these learned relationships in applying an additional layer of attention processing to augment an encoding of the embedding of tokens in determining likelihoods of applicability $y_1$ through $y_{n_y}$.

According to an embodiment, convoluted embedding 252 may transform individual tokens $x_1$ through $x_{n_x}$ to an embedding of tokens of a dimension d using an embedding layer followed by two one-dimensional convolutional neural network (CNN) layers. Like in the embedding of tokens in as described in connection with FIG. 2A, $E_x$ may comprise a matrix of context values where a row of $E_x$ may map to corresponding service codes and where a context value $E_x(i,j)$ maps a token i to a service code j.

In a particular implementation, an application of CNN layers may preprocess tokens $x_1$ through $x_{n_x}$ to associate related tokens (e.g., tokens that are in proximity in a sentence and/or adjacent sentences) tokens (like n-grams) in a convoluted embedding of tokens corresponding to tokens $x_1$ through $x_{n_x}$. In an implementation, such a convoluted embedding of tokens corresponding to tokens $x_1$ through $x_{n_x}$ may be based, least in part, on local semantic dependencies (e.g., semantic dependencies of tokens in a grammatically correct sentence) in clinical notes. $E_x$ may comprise a two-dimensional matrix to express such an embedding of tokens where vectors $E_{x,1}$ through $E_{x,n_x}$ may comprise components of $E_x$.

According to an embodiment, convoluted embedding 252 may execute a pre-training process to learn associations between and/or among tokens in a vocabulary of tokens 1 through $n_x$ defining tokens $x_1$ through $x_{n_x}$ (e.g., $n_x$=4096). Such associations may reflect similarities between and/or among tokens in a semantic/linguistic vector space defined, for example, by dependencies of tokens within a sentence or adjacent sentences, semantic/linguistic similarities, just to provide a couple of examples. In a particular implementation, such a pre-training process may be implemented as a Word2vec process using a Skip-gram model. Here, such a model may be trained to generate an embedding such as an embedding of size d=300, a window size five for multiple training epochs with sample tokenized sets of clinical notes. It should be understood, however, that these are merely example values/parameters to define a pre-training process for a particular implementation, and claimed subject matter is not limited in this respect.

An initial embedding generated by a Word2vec process may define pretrained weights to be loaded to an additional embedding layer comprising two CNN layers with d filters, kernel size ten, for example. Here, two CNN layers of convoluted embedding 252 may process tokens $x_1$ through $x_{n_x}$ to provide output values. In one implementation, the two CNN layers may apply a dropout to the output values of about 10%, for example. A suitable activation function (e.g., tanh or other suitable activation function) may be applied to such output values to provide context values of $E_x$.

According to an embodiment, self-attention 256 may generate an attention-mapped embedding of tokens $U_x$ based, at least in part, on an embedding of tokens expressed in $E_x$ (generated by convoluted embedding 252). Self-attention 256 may apply a multiple-layered model such as a stack of four identical layers. In an implementation, a single layer in such a multiple-layered model may comprise single-head self-attention and feed-forward layers interleaved with residual connections and layer normalization. In a particular implementation, $E_x$ generated by convoluted embedding 252 may map each token $x_1$ through $x_{n_x}$ to a corresponding vector of context values of length d. Based, at least in part, on these vectors expressed in $E_x$, according to an embodiment, self-attention 256 may associate different tokens embedded in a sequence as expressed in $E_x$ to improve a tokenized encoding of clinical notes, for example.

According to an embodiment, a degree of self-attention of an embedding of tokens may be expressed in three vectors corresponding to "query," "key" and "value." In an implementation, such query, key and value components of an embedding of tokens $E_x$ may be expressed by application of projection matrices in a multi-layered model. Such a multiple-layered model may be implemented by application of projection matrices $W_q$, $W_k$, $W_v \in \mathbb{R}^{d \times d}$, corresponding to query, key and value vectors, respectively, according to expression (2) as follows:

$$\text{Attn}(E_x) = \text{LN}\left\{E_x + \text{Softmax}\left[\frac{(E_xW_q)(E_xW_k)^T}{\sqrt{d}}\right](E_xW_v)\right\}, \quad (2)$$

where:
Softmax is a function to map values to real numbers in a range between zero and one (e.g., to represent likelihoods and/or probabilities); and LN(Z) is a layer normalization function.

In an embodiment, layer normalization function LN(Z) may weight values in vectors of matrix Z so as to normalize to common statistical attributes such as mean and variance, for example. Self-attention 256 may then implement a feed forward neural network to determine attention-mapped embedding of tokens $U_x$ according to expression (3) as follows:

$$U_{x,i} = \text{FFN}(E_{x,i}) = \text{LN}\{\text{Attn}(E_{x,i}) + \delta[\text{Attn}(E_{x,i})W_1]W_2\}, \quad (3)$$

where:

$W_1 \in \mathbb{R}^{d \times d_{ff}}$ and $W_2 \in \mathbb{R}^{d_{ff} \times d}$; and δ is an ReLU activation function.

In a particular implementation, $d_{ff}=1024$. But embodiments are not limited to this particular implementation. A dropout to each sublayer output may occur prior to such a sublayer output being added to sub-layer input with a normalization rate of 0.1.

According to an embodiment, code-title embedding 262 may learn interrelationships between and/or among code titles to be expressed in an extracted code-title embedding matrix $E_t \in \mathbb{R}^{n_y \times d}$. In the particular implementation, code titles corresponding with service codes may be defined according to a well-established set of service codes such as, for example, service codes defined by International Classification of Disease (ICD) coding systems. Such code titles may comprise text that uniquely identifies and/or is descriptive of services underlying associated service codes. Such code titles may include, for example, "gastric intubation" (43752, 91105); "interpretation of blood gases and interpretation of data stored in computers, such as ECGs, blood pressure, hematologic data" (99090); "interpretation of cardiac output" (93561-93562); "interpretation of chest X-rays" (71010-71020); "pulse oximetry" (94760-94762); "temporary transcutaneous pacing" (92953); "vascular access procedures" (36000, 36410, 36415, 36591, 36600); and "ventilator management" (94002-94004, 94660, 94662). In particular embodiments, service codes may be rare (aka "tail"). In particular implementations, application of code-title embedding 262 may enable a learning of semantic patterns and/or relationships between and/or among code titles that improves accuracy of code prediction.

According to an embodiment, code-title guided attention 260 may determine likelihoods of code applicability $y_1$ through $y_{n_y}$ based, at least in part, on attention-mapped embedding of tokens $U_x$ (e.g., as determined by self-attention 256). In a particular implementation, code-title guided attention 260 incorporates associations between and/or among different service code titles (e.g., clinical service code titles) 1 through $n_y$ in determining corresponding likelihood values $y_1$ through $y_{n_y}$. For example, code-title guided attention 260 may apply recognized and/or learned interrelationship between and/or among different service code titles, such as interrelationships between and/or among titles less frequently applied service codes, in determining likelihoods of code applicability $y_1$ through $y_{n_y}$.

According to an embodiment, like clinical nodes as discussed above, code-title embedding 262 may express context values associated with service codes 1 through $n_y$ in a vocabulary of Z tokens. Additionally, code-title embedding 262 may determine a tokenization corresponding to service codes 1 through $n_y$ where a tokenization of such codes 1 through $n_y$ in a matrix $T \in \mathbb{R}^{n_y \times Z}$. Additionally, code-title embedding 262 may determine an embedding of such tokens to express context values associated with service code titles corresponding to service codes 1 through $n_y$ in a matrix $T \in \mathbb{R}^{n_y \times Z}$. Based, at least in part, on matrix T code-title embedding 262 may determine an extracted code-title embedding matrix $E_t \in \mathbb{R}^{n_y \times d}$ having context values to be applied by code-title guided attention 260 to attention-mapped embedding of tokens $U_x$.

According to an embodiment, for each code title to be associated with context values in matrix $E_t$, in a particular implementation, matrix $E_t$ may include a padding of $n_t$ number of elements (e.g., $n_t=36$). Code-title embedding 262 may apply pretrained Word2vec Skip-gram model weights determined by convoluted embedding 252 and/or apply weights derived from such model weights determined by convoluted embedding 252 to initialize an embedding layer comprising a single CNN layer with d=300 filters and kernel size ten, for example. A suitable activation function (e.g., tanh or other suitable activation function) may then be applied to such output values to provide coefficients of $E_t$. Based, at least in part, on learned relationships between and/or among different service code titles determined by code-title embedding 262, code-title guided attention 260 may apply a subsequent attention mapping to attention mapped embedding of tokens $U_x$. Here, an extracted code-title embedding matrix $E_t \in \mathbb{R}^{n_y \times d}$ may be applied as a query matrix to guide attention from token embeddings in expression (4) as follows:

$$V_x = \text{Softmax}\left(\frac{E_t U_x^T}{\sqrt{d}}\right) U_x, \quad (4)$$

where $V_x \in \mathbb{R}^{n_y \times d}$.

As such, attention scores are computed based, at least in part, on corresponding dot products implemented according to the expression $E_t U_x^T$. According to an embodiment, recognizing particular queries that are close in Euclidean space having similar attention scores may enable efficient learning interrelations between and/or among less frequently applied service codes and text. Such a Euclidean space may define one or more query dimensions, for example. Here, $E_t$ may be implemented as a query in the computation of attention scores in $V_x$ to achieve significant performance gains. Finally, likelihoods of applicability of service codes may be computed by code-title guided attention 260 according to expression (5) as follows:

$$y = \sigma(V_x W_3), \quad (5)$$

where $W_3 \in \mathbb{R}^{d \times 1}$ and σ is a sigmoid function.

According to an embodiment, parameters to implement convoluted embedding 252, self-attention 256, code-title guided attention 260 and code-title embedding 262 (e.g., coefficients for $W_1, W_2, W_3, W_v, W_q, W_k, E_t$) may be trained over multiple training samples and/or epochs. In a particular implementation, training samples may be generated for multiple permutations of linguistic elements of a clinical note. For a clinical note including multiple sentences, for example, a training scheme may employ permutation equivariance to randomly shuffle an ordering of such multiple sentences to spawn new training sequences. It has been shown, for example, that a three-fold augmentation of a single note to generate three corresponding sets of training samples may significantly enhance accuracy of determining likelihoods of applicability $y_1$ through $y_{n_y}$. In another implementation, an entirety of convoluted embedding 252, self-attention 256, code-title guided attention 260 and code-title embedding 262 may be trained on a set of medical codes to maximize a log-likelihood of binary classifiers 1 through $n_y$. Here, a stochastic weighted averaging (SWA) be used to store a running average of model weights in a training sequence. In a particular example, an SWA may be averaged every five epochs staring with an initial epoch. This may improve speed and accuracy of prediction over conventional ensemble techniques.

Figure 3:
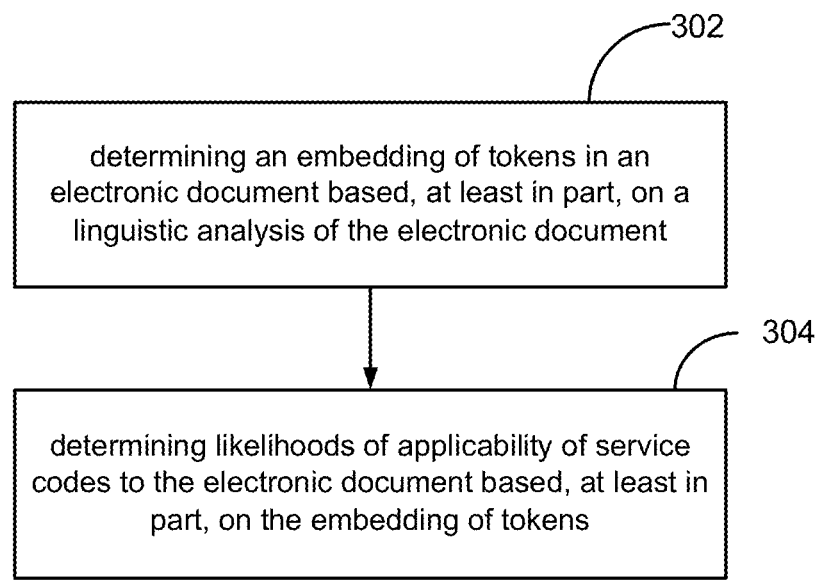
FIG. 3 is a flow diagram of a process to determine service codes based on an electronic document, according to an embodiment.

FIG. 3 is a flow diagram of a process to determine service codes based on an electronic document, according to an embodiment. Such an electronic document may comprise notes and/or text relating to a clinical diagnosis and/or service such as electronic document 104. Block 302 may comprise determination of an embedding of tokens, such as an embedding of tokens 204 and/or 254 ($E_x$) discussed above. In this context, a "token" as referred to herein means a linguistic component of a sentence and/or other linguistic expression. In a particular example, and as discussed herein, an analysis of a linguistic sample (e.g., text) may be mapped to tokens from among a finite set of tokens defining a vocabulary of tokens. In a particular example discussed herein, such a vocabulary of tokens may be selected/determined according to particular identifiable services associated with service codes. In particular implementations, block 302 may determine an embedding of tokens in a vocabulary of tokens greater than 4096 tokens. An "embedding" of tokens as referred to herein means an expression of a mapping of tokens to a collection of words expressing a thought, sentence, portion of a sentence or other linguistic expression. In particular examples discussed herein, such an embedding of tokens may be determined, computed and/or generated according to one or more BERT transformers and/or multi-level CNNs, just to provide a couple of examples of techniques that may be used to compute an embedding of tokens.

Block 304 may comprise determining likelihoods of applicability of service codes to an electronic document. In this context, a "service code" as referred to herein means a code (e.g., alphanumeric code) and/or symbol representing a defined service. In particular examples discussed herein, such a defined service may comprise a service provided by a medical service provider. In other implementations, such a defined service may comprise different types of services provided by different kinds of service providers. As pointed out above, block 304 may determine likelihoods of applicability of service codes as $y_i$ according expression (1) or (5), for example. Also, as discussed above likelihoods of applicability of service codes as $y_i$ according to expression (5) may involve determining a tokenization of code titles and an embedding of such a tokenization of code titles.

As discussed above, CAC techniques may be unable to handle increasingly complex and increasingly numerous medical codes. A technical solution of embedding a "tokenization" of medical notes (e.g., "charts") and an application of an attention model may enable automated generation of service codes selected from a large number of service codes (e.g., up to 68,000 diagnosis codes and service codes or more). In a particular, as discussed herein, computing an embedding of tokens (e.g., an embedding of tokenized clinical notes and/or code titles using techniques discussed herein) and/or an application of an attention mapping may provide a technical solution to improve operation of computing devices employed in automated clinical coding (ACC) and/or computer assisted coding (CAC) to improve accuracy and/or throughput. It should be appreciated that a computational complexity of tokenizing content such as clinical notes and/or code titles precludes from performing such a tokenization in a human mind or with pencil and paper, as a practical matter. For example, specific techniques to determine an embedding of tokens (e.g., in the firm of a matrix of context values associated with tokens in a vocabulary of tokens) based on linguistic content determined from a bidirectional encoder representations from transformers and/or convolutional neural networks are of a complexity that cannot practically be performed in the human mind. Likewise, computation of a tokenization of code titles, embedding of such a tokenization of code titles, and application of such an embedding of tokenized code titles using convolutional neural networks cannot practically be performed in the human mind. Additional techniques to determine likelihoods of applicability of service codes by application of an attention model to an embedding of tokens introduces even more computational complexity that cannot be performed in a human mind.

It should also be understood that the process of FIG. 3 has several practical applications in the fields of mapping notes or contact to service codes such as, for example, the practical application of processing medical/clinical notes to medical service codes with improved accuracy. Indeed, techniques disclosed herein have shown to provide substantial benefits in improved accuracy over use of over the use of human coders alone. More efficient techniques to process notes gathered in an electronic format to provide service codes for electronic billing. Requiring less human operator interaction.

In the context of the present patent application, the term "connection," the term "component" and/or similar terms are intended to be physical, but are not necessarily always tangible. Whether or not these terms refer to tangible subject matter, thus, may vary in a particular context of usage. As an example, a tangible connection and/or tangible connection path may be made, such as by a tangible, electrical connection, such as an electrically conductive path comprising metal or other conductor, that is able to conduct electrical current between two tangible components. Likewise, a tangible connection path may be at least partially affected and/or controlled, such that, as is typical, a tangible connection path may be open or closed, at times resulting from influence of one or more externally derived signals, such as external currents and/or voltages, such as for an electrical switch. Non-limiting illustrations of an electrical switch include a transistor, a diode, etc. However, a "connection" and/or "component," in a particular context of usage, likewise, although physical, can also be non-tangible, such as a connection between a client and a server over a network, particularly a wireless network, which generally refers to the ability for the client and server to transmit, receive, and/or exchange communications, as discussed in more detail later.

In a particular context of usage, such as a particular context in which tangible components are being discussed, therefore, the terms "coupled" and "connected" are used in a manner so that the terms are not synonymous. Similar terms may also be used in a manner in which a similar intention is exhibited. Thus, "connected" is used to indicate that two or more tangible components and/or the like, for example, are tangibly in direct physical contact. Thus, using the previous example, two tangible components that are electrically connected are physically connected via a tangible electrical connection, as previously discussed. However, "coupled," is used to mean that potentially two or more tangible components are tangibly in direct physical contact. Nonetheless, "coupled" is also used to mean that two or more tangible components and/or the like are not necessarily tangibly in direct physical contact, but are able to co-operate, liaise, and/or interact, such as, for example, by being "optically coupled." Likewise, the term "coupled" is also understood to mean indirectly connected. It is further noted, in the context of the present patent application, since memory, such as a memory component and/or memory states, is intended to be non-transitory, the term physical, at least if used in relation to memory necessarily implies that such memory components and/or memory states, continuing with the example, are tangible.

Additionally, in the present patent application, in a particular context of usage, such as a situation in which tangible components (and/or similarly, tangible materials) are being discussed, a distinction exists between being "on" and being "over." As an example, deposition of a substance "on" a substrate refers to a deposition involving direct physical and tangible contact without an intermediary, such as an intermediary substance, between the substance deposited and the substrate in this latter example; nonetheless, deposition "over" a substrate, while understood to potentially include deposition "on" a substrate (since being "on" may also accurately be described as being "over"), is understood to include a situation in which one or more intermediaries, such as one or more intermediary substances, are present between the substance deposited and the substrate so that the substance deposited is not necessarily in direct physical and tangible contact with the substrate.

A similar distinction is made in an appropriate particular context of usage, such as in which tangible materials and/or tangible components are discussed, between being "beneath" and being "under." While "beneath," in such a particular context of usage, is intended to necessarily imply physical and tangible contact (similar to "on," as just described), "under" potentially includes a situation in which there is direct physical and tangible contact, but does not necessarily imply direct physical and tangible contact, such as if one or more intermediaries, such as one or more intermediary substances, are present. Thus, "on" is understood to mean "immediately over" and "beneath" is understood to mean "immediately under."

It is likewise appreciated that terms such as "over" and "under" are understood in a similar manner as the terms "up," "down," "top," "bottom," and so on, previously mentioned. These terms may be used to facilitate discussion, but are not intended to necessarily restrict scope of claimed subject matter. For example, the term "over," as an example, is not meant to suggest that claim scope is limited to only situations in which an embodiment is right side up, such as in comparison with the embodiment being upside down, for example. An example includes a flip chip, as one illustration, in which, for example, orientation at various times (e.g., during fabrication) may not necessarily correspond to orientation of a final product. Thus, if an object, as an example, is within applicable claim scope in a particular orientation, such as upside down, as one example, likewise, it is intended that the latter also be interpreted to be included within applicable claim scope in another orientation, such as right side up, again, as an example, and vice-versa, even if applicable literal claim language has the potential to be interpreted otherwise. Of course, again, as always has been the case in the specification of a patent application, particular context of description and/or usage provides helpful guidance regarding reasonable inferences to be drawn.

Unless otherwise indicated, in the context of the present patent application, the term "or" if used to associate a list, such as A, B, or C, is intended to mean A, B, and C, here used in the inclusive sense, as well as A, B, or C, here used in the exclusive sense. With this understanding, "and" is used in the inclusive sense and intended to mean A, B, and C; whereas "and/or" can be used in an abundance of caution to make clear that all of the foregoing meanings are intended, although such usage is not required. In addition, the term "one or more" and/or similar terms is used to describe any feature, structure, characteristic, and/or the like in the singular, "and/or" is also used to describe a plurality and/or some other combination of features, structures, characteristics, and/or the like. Likewise, the term "based on" and/or similar terms are understood as not necessarily intending to convey an exhaustive list of factors, but to allow for existence of additional factors not necessarily expressly described.

Furthermore, it is intended, for a situation that relates to implementation of claimed subject matter and is subject to testing, measurement, and/or specification regarding degree, that the particular situation be understood in the following manner. As an example, in a given situation, assume a value of a physical property is to be measured. If alternatively reasonable approaches to testing, measurement, and/or specification regarding degree, at least with respect to the property, continuing with the example, is reasonably likely to occur to one of ordinary skill, at least for implementation purposes, claimed subject matter is intended to cover those alternatively reasonable approaches unless otherwise expressly indicated. As an example, if a plot of measurements over a region is produced and implementation of claimed subject matter refers to employing a measurement of slope over the region, but a variety of reasonable and alternative techniques to estimate the slope over that region exist, claimed subject matter is intended to cover those reasonable alternative techniques unless otherwise expressly indicated.

To the extent claimed subject matter is related to one or more particular measurements, such as with regard to physical manifestations capable of being measured physically, such as, without limit, temperature, pressure, voltage, current, electromagnetic radiation, etc., it is believed that claimed subject matter does not fall within the abstract idea judicial exception to statutory subject matter. Rather, it is asserted, that physical measurements are not mental steps and, likewise, are not abstract ideas.

It is noted, nonetheless, that a typical measurement model employed is that one or more measurements may respectively comprise a sum of at least two components. Thus, for a given measurement, for example, one component may comprise a deterministic component, which in an ideal sense, may comprise a physical value (e.g., sought via one or more measurements), often in the form of one or more signals, signal samples and/or states, and one component may comprise a random component, which may have a variety of sources that may be challenging to quantify. At times, for example, lack of measurement precision may affect a given measurement. Thus, for claimed subject matter, a statistical or stochastic model may be used in addition to a deterministic model as an approach to identification and/or prediction regarding one or more measurement values that may relate to claimed subject matter.

For example, a relatively large number of measurements may be collected to better estimate a deterministic component. Likewise, if measurements vary, which may typically occur, it may be that some portion of a variance may be explained as a deterministic component, while some portion of a variance may be explained as a random component. Typically, it is desirable to have stochastic variance associated with measurements be relatively small, if feasible. That is, typically, it may be preferable to be able to account for a reasonable portion of measurement variation in a deterministic manner, rather than a stochastic matter as an aid to identification and/or predictability.

Along these lines, a variety of techniques have come into use so that one or more measurements may be processed to better estimate an underlying deterministic component, as well as to estimate potentially random components. These techniques, of course, may vary with details surrounding a given situation. Typically, however, more complex problems may involve use of more complex techniques. In this regard, as alluded to above, one or more measurements of physical manifestations may be modelled deterministically and/or stochastically. Employing a model permits collected measurements to potentially be identified and/or processed, and/or potentially permits estimation and/or prediction of an underlying deterministic component, for example, with respect to later measurements to be taken. A given estimate may not be a perfect estimate; however, in general, it is expected that on average one or more estimates may better reflect an underlying deterministic component, for example, if random components that may be included in one or more obtained measurements, are considered. Practically speaking, of course, it is desirable to be able to generate, such as through estimation approaches, a physically meaningful model of processes affecting measurements to be taken.

In some situations, however, as indicated, potential influences may be complex. Therefore, seeking to understand appropriate factors to consider may be particularly challenging. In such situations, it is, therefore, not unusual to employ heuristics with respect to generating one or more estimates. Heuristics refers to use of experience related approaches that may reflect realized processes and/or realized results, such as with respect to use of historical measurements, for example. Heuristics, for example, may be employed in situations where more analytical approaches may be overly complex and/or nearly intractable. Thus, regarding claimed subject matter, an innovative feature may include, in an example embodiment, heuristics that may be employed, for example, to estimate and/or predict one or more measurements.

A "signal measurement" and/or a "signal measurement vector" may be referred to respectively as a "random measurement" and/or a "random vector," such that the term "random" may be understood in context with respect to the fields of probability, random variables and/or stochastic processes. A random vector may be generated by having measurement signal components comprising one or more random variables. Random variables may comprise signal value measurements, which may, for example, be specified in a space of outcomes. Thus, in some contexts, a probability (e.g., likelihood) may be assigned to outcomes, as often may be used in connection with approaches employing probability and/or statistics. In other contexts, a random variable may be substantially in accordance with a measurement comprising a deterministic measurement value or, perhaps, an average measurement component plus random variation about a measurement average.

The terms "correspond", "reference", "associate", and/or similar terms relate to signals, signal samples and/or states, e.g., components of a signal measurement vector, which may be stored in memory and/or employed with operations to generate results, depending, at least in part, on the above-mentioned, signal samples and/or signal sample states. For example, a signal sample measurement vector may be stored in a memory location and further referenced wherein such a reference may be embodied and/or described as a stored relationship. A stored relationship may be employed by associating (e.g., relating) one or more memory addresses to one or more another memory addresses, for example, and may facilitate an operation, involving, at least in part, a combination of signal samples and/or states stored in memory, such as for processing by a processor and/or similar device, for example. Thus, in a particular context, "associating," "referencing," and/or "corresponding" may, for example, refer to an executable process of accessing memory contents of two or more memory locations, e.g., to facilitate execution of one or more operations among signal samples and/or states, wherein one or more results of the one or more operations may likewise be employed for additional processing, such as in other operations, or may be stored in the same or other memory locations, as may, for example, be directed by executable instructions. Furthermore, terms "fetching" and "reading" or "storing" and "writing" are to be understood as interchangeable terms for the respective operations, e.g., a result may be fetched (or read) from a memory location; likewise, a result may be stored in (or written to) a memory location.

It is further noted that the terms "type" and/or "like," if used, such as with a feature, structure, characteristic, and/or the like, using "optical" or "electrical" as simple examples, means at least partially of and/or relating to the feature, structure, characteristic, and/or the like in such a way that presence of minor variations, even variations that might otherwise not be considered fully consistent with the feature, structure, characteristic, and/or the like, do not in general prevent the feature, structure, characteristic, and/or the like from being of a "type" and/or being "like," (such as being an "optical-type" or being "optical-like," for example) if the minor variations are sufficiently minor so that the feature, structure, characteristic, and/or the like would still be considered to be substantially present with such variations also present. Thus, continuing with this example, the terms optical-type and/or optical-like properties are necessarily intended to include optical properties. Likewise, the terms electrical-type and/or electrical-like properties, as another example, are necessarily intended to include electrical properties. It should be noted that the specification of the present patent application merely provides one or more illustrative examples and claimed subject matter is intended to not be limited to one or more illustrative examples; however, again, as has always been the case with respect to the specification of a patent application, particular context of description and/or usage provides helpful guidance regarding reasonable inferences to be drawn.

With advances in technology, it has become more typical to employ distributed computing and/or communication approaches in which portions of a process, such as signal processing of signal samples, for example, may be allocated among various devices, including one or more client devices and/or one or more server devices, via a computing and/or communications network, for example. A network may comprise two or more devices, such as network devices and/or computing devices, and/or may couple devices, such as network devices and/or computing devices, so that signal communications, such as in the form of signal packets and/or signal frames (e.g., comprising one or more signal samples), for example, may be exchanged, such as between a server device and/or a client device, as well as other types of devices, including between wired and/or wireless devices coupled via a wired and/or wireless network, for example.

An example of a distributed computing system comprises the so-called Hadoop distributed computing system, which employs a map-reduce type of architecture. In the context of the present patent application, the terms map-reduce architecture and/or similar terms are intended to refer to a distributed computing system implementation and/or embodiment for processing and/or for generating larger sets of signal samples employing map and/or reduce operations for a parallel, distributed process performed over a network of devices. A map operation and/or similar terms refer to processing of signals (e.g., signal samples) to generate one or more key-value pairs and to distribute the one or more pairs to one or more devices of the system (e.g., network). A reduce operation and/or similar terms refer to processing of signals (e.g., signal samples) via a summary operation (e.g., such as counting the number of students in a queue, yielding name frequencies, etc.). A system may employ such an architecture, such as by marshaling distributed server devices, executing various tasks in parallel, and/or managing communications, such as signal transfers, between various parts of the system (e.g., network), in an embodiment. As mentioned, one non-limiting, but well-known, example comprises the Hadoop distributed computing system. It refers to an open source implementation and/or embodiment of a map-reduce type architecture (available from the Apache Software Foundation, 1901 Munsey Drive, Forrest Hill, MD, 21050-2747), but may include other aspects, such as the Hadoop distributed file system (HDFS) (available from the Apache Software Foundation, 1901 Munsey Drive, Forrest Hill, MD, 21050-2747). In general, therefore, "Hadoop" and/or similar terms (e.g., "Hadoop-type," etc.) refer to an implementation and/or embodiment of a scheduler for executing larger processing jobs using a map-reduce architecture over a distributed system. Furthermore, in the context of the present patent application, use of the term "Hadoop" is intended to include versions, presently known and/or to be later developed.

In the context of the present patent application, the term network device refers to any device capable of communicating via and/or as part of a network and may comprise a computing device. While network devices may be capable of communicating signals (e.g., signal packets and/or frames), such as via a wired and/or wireless network, they may also be capable of performing operations associated with a computing device, such as arithmetic and/or logic operations, processing and/or storing operations (e.g., storing signal samples), such as in memory as tangible, physical memory states, and/or may, for example, operate as a server device and/or a client device in various embodiments. Network devices capable of operating as a server device, a client device and/or otherwise, may include, as examples, dedicated rack-mounted servers, desktop computers, laptop computers, set top boxes, tablets, netbooks, smart phones, wearable devices, integrated devices combining two or more features of the foregoing devices, and/or the like, or any combination thereof. As mentioned, signal packets and/or frames, for example, may be exchanged, such as between a server device and/or a client device, as well as other types of devices, including between wired and/or wireless devices coupled via a wired and/or wireless network, for example, or any combination thereof. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases and/or portions thereof, as appropriate.

It should be understood that for ease of description, a network device (also referred to as a networking device) may be embodied and/or described in terms of a computing device and vice-versa. However, it should further be understood that this description should in no way be construed so that claimed subject matter is limited to one embodiment, such as only a computing device and/or only a network device, but, instead, may be embodied as a variety of devices or combinations thereof, including, for example, one or more illustrative examples.

A network may also include now known, and/or to be later developed arrangements, derivatives, and/or improvements, including, for example, past, present and/or future mass storage, such as network attached storage (NAS), a storage area network (SAN), and/or other forms of device readable media, for example. A network may include a portion of the Internet, one or more local area networks (LANs), one or more wide area networks (WANs), wire-line type connections, wireless type connections, other connections, or any combination thereof. Thus, a network may be worldwide in scope and/or extent. Likewise, sub-networks, such as may employ differing architectures and/or may be substantially compliant and/or substantially compatible with differing protocols, such as network computing and/or communications protocols (e.g., network protocols), may interoperate within a larger network.

In the context of the present patent application, the term sub-network and/or similar terms, if used, for example, with respect to a network, refers to the network and/or a part thereof. Sub-networks may also comprise links, such as physical links, connecting and/or coupling nodes, so as to be capable to communicate signal packets and/or frames between devices of particular nodes, including via wired links, wireless links, or combinations thereof. Various types of devices, such as network devices and/or computing devices, may be made available so that device interoperability is enabled and/or, in at least some instances, may be transparent. In the context of the present patent application, the term "transparent," if used with respect to devices of a network, refers to devices communicating via the network in which the devices are able to communicate via one or more intermediate devices, such as one or more intermediate nodes, but without the communicating devices necessarily specifying the one or more intermediate nodes and/or the one or more intermediate devices of the one or more intermediate nodes and/or, thus, may include within the network the devices communicating via the one or more intermediate nodes and/or the one or more intermediate devices of the one or more intermediate nodes, but may engage in signal communications as if such intermediate nodes and/or intermediate devices are not necessarily involved. For example, a router may provide a link and/or connection between otherwise separate and/or independent LANs.

In the context of the present patent application, a "private network" refers to a particular, limited set of devices, such as network devices and/or computing devices, able to communicate with other devices, such as network devices and/or computing devices, in the particular, limited set, such as via signal packet and/or signal frame communications, for example, without a need for re-routing and/or redirecting signal communications. A private network may comprise a stand-alone network; however, a private network may also comprise a subset of a larger network, such as, for example, without limitation, all or a portion of the Internet. Thus, for example, a private network "in the cloud" may refer to a private network that comprises a subset of the Internet. Although signal packet and/or frame communications (e.g. signal communications) may employ intermediate devices of intermediate nodes to exchange signal packets and/or signal frames, those intermediate devices may not necessarily be included in the private network by not being a source or designated destination for one or more signal packets and/or signal frames, for example. It is understood in the context of the present patent application that a private network may direct outgoing signal communications to devices not in the private network, but devices outside the private network may not necessarily be able to direct inbound signal communications to devices included in the private network.

The Internet refers to a decentralized global network of interoperable networks that comply with the Internet Protocol (IP). It is noted that there are several versions of the Internet Protocol. The term Internet Protocol, IP, and/or similar terms are intended to refer to any version, now known and/or to be later developed. The Internet includes local area networks (LANs), wide area networks (WANs), wireless networks, and/or long haul public networks that, for example, may allow signal packets and/or frames to be communicated between LANs. The term World Wide Web (WWW or Web) and/or similar terms may also be used, although it refers to a part of the Internet that complies with the Hypertext Transfer Protocol (HTTP). For example, network devices may engage in an HTTP session through an exchange of appropriately substantially compatible and/or substantially compliant signal packets and/or frames. It is noted that there are several versions of the Hypertext Transfer Protocol. The term Hypertext Transfer Protocol, HTTP, and/or similar terms are intended to refer to any version, now known and/or to be later developed. It is likewise noted that in various places in this document substitution of the term Internet with the term World Wide Web ("Web") may be made without a significant departure in meaning and may, therefore, also be understood in that manner if the statement would remain correct with such a substitution.

Although claimed subject matter is not in particular limited in scope to the Internet and/or to the Web; nonetheless, the Internet and/or the Web may without limitation provide a useful example of an embodiment at least for purposes of illustration. As indicated, the Internet and/or the Web may comprise a worldwide system of interoperable networks, including interoperable devices within those networks. The Internet and/or Web has evolved to a public, self-sustaining facility accessible to potentially billions of people or more worldwide. Also, in an embodiment, and as mentioned above, the terms "WWW" and/or "Web" refer to a part of the Internet that complies with the Hypertext Transfer Protocol. The Internet and/or the Web, therefore, in the context of the present patent application, may comprise a service that organizes stored digital content, such as, for example, text, images, video, etc., through the use of hypermedia, for example. It is noted that a network, such as the Internet and/or Web, may be employed to store electronic files and/or electronic documents.

The term electronic file and/or the term electronic document are used throughout this document to refer to a set of stored memory states and/or a set of physical signals associated in a manner so as to thereby at least logically form a file (e.g., electronic) and/or an electronic document. That is, it is not meant to implicitly reference a particular syntax, format and/or approach used, for example, with respect to a set of associated memory states and/or a set of associated physical signals. If a particular type of file storage format and/or syntax, for example, is intended, it is referenced expressly. It is further noted an association of memory states, for example, may be in a logical sense and not necessarily in a tangible, physical sense. Thus, although signal and/or state components of a file and/or an electronic document, for example, are to be associated logically, storage thereof, for example, may reside in one or more different places in a tangible, physical memory, in an embodiment.

A Hyper Text Markup Language ("HTML"), for example, may be utilized to specify digital content and/or to specify a format thereof, such as in the form of an electronic file and/or an electronic document, such as a Web page, Web site, etc., for example. An Extensible Markup Language ("XML") may also be utilized to specify digital content and/or to specify a format thereof, such as in the form of an electronic file and/or an electronic document, such as a Web page, Web site, etc., in an embodiment. Of course, HTML and/or XML are merely examples of "markup" languages, provided as non-limiting illustrations. Furthermore, HTML and/or XML are intended to refer to any version, now known and/or to be later developed, of these languages. Likewise, claimed subject matter are not intended to be limited to examples provided as illustrations, of course.

In the context of the present patent application, the term "Web site" and/or similar terms refer to Web pages that are associated electronically to form a particular collection thereof. Also, in the context of the present patent application, "Web page" and/or similar terms refer to an electronic file and/or an electronic document accessible via a network, including by specifying a uniform resource locator (URL) for accessibility via the Web, in an example embodiment. As alluded to above, in one or more embodiments, a Web page may comprise digital content coded (e.g., via computer instructions) using one or more languages, such as, for example, markup languages, including HTML and/or XML, although claimed subject matter is not limited in scope in this respect. Also, in one or more embodiments, application developers may write code (e.g., computer instructions) in the form of JavaScript (or other programming languages), for example, executable by a computing device to provide digital content to populate an electronic document and/or an electronic file in an appropriate format, such as for use in a particular application, for example. Use of the term "JavaScript" and/or similar terms intended to refer to one or more particular programming languages are intended to refer to any version of the one or more programming languages identified, now known and/or to be later developed. Thus, JavaScript is merely an example programming language. As was mentioned, claimed subject matter is not intended to be limited to examples and/or illustrations.

In the context of the present patent application, the terms "entry," "electronic entry," "document," "electronic document," "content", "digital content," "item," and/or similar terms are meant to refer to signals and/or states in a physical format, such as a digital signal and/or digital state format, e.g., that may be perceived by a user if displayed, played, tactilely generated, etc. and/or otherwise executed by a device, such as a digital device, including, for example, a computing device, but otherwise might not necessarily be readily perceivable by humans (e.g., if in a digital format). Likewise, in the context of the present patent application, digital content provided to a user in a form so that the user is able to readily perceive the underlying content itself (e.g., content presented in a form consumable by a human, such as hearing audio, feeling tactile sensations and/or seeing images, as examples) is referred to, with respect to the user, as "consuming" digital content, "consumption" of digital content, "consumable" digital content and/or similar terms. For one or more embodiments, an electronic document and/or an electronic file may comprise a Web page of code (e.g., computer instructions) in a markup language executed or to be executed by a computing and/or networking device, for example. In another embodiment, an electronic document and/or electronic file may comprise a portion and/or a region of a Web page. However, claimed subject matter is not intended to be limited in these respects.

Also, for one or more embodiments, an electronic document and/or electronic file may comprise a number of components. As previously indicated, in the context of the present patent application, a component is physical, but is not necessarily tangible. As an example, components with reference to an electronic document and/or electronic file, in one or more embodiments, may comprise text, for example, in the form of physical signals and/or physical states (e.g., capable of being physically displayed). Typically, memory states, for example, comprise tangible components, whereas physical signals are not necessarily tangible, although signals may become (e.g., be made) tangible, such as if appearing on a tangible display, for example, as is not uncommon. Also, for one or more embodiments, components with reference to an electronic document and/or electronic file may comprise a graphical object, such as, for example, an image, such as a digital image, and/or sub-objects, including attributes thereof, which, again, comprise physical signals and/or physical states (e.g., capable of being tangibly displayed). In an embodiment, digital content may comprise, for example, text, images, audio, video, and/or other types of electronic documents and/or electronic files, including portions thereof, for example.

Also, in the context of the present patent application, the term parameters (e.g., one or more parameters) refer to material descriptive of a collection of signal samples, such as one or more electronic documents and/or electronic files, and exist in the form of physical signals and/or physical states, such as memory states. For example, one or more parameters, such as referring to an electronic document and/or an electronic file comprising an image, may include, as examples, time of day at which an image was captured, latitude and longitude of an image capture device, such as a camera, for example, etc. In another example, one or more parameters relevant to digital content, such as digital content comprising a technical article, as an example, may include one or more authors, for example. Claimed subject matter is intended to embrace meaningful, descriptive parameters in any format, so long as the one or more parameters comprise physical signals and/or states, which may include, as parameter examples, collection name (e.g., electronic file and/or electronic document identifier name), technique of creation, purpose of creation, time and date of creation, logical path if stored, coding formats (e.g., type of computer instructions, such as a markup language) and/or standards and/or specifications used so as to be protocol compliant (e.g., meaning substantially compliant and/or substantially compatible) for one or more uses, and so forth.

Signal packet communications and/or signal frame communications, also referred to as signal packet transmissions and/or signal frame transmissions (or merely "signal packets" or "signal frames"), may be communicated between nodes of a network, where a node may comprise one or more network devices and/or one or more computing devices, for example. As an illustrative example, but without limitation, a node may comprise one or more sites employing a local network address, such as in a local network address space. Likewise, a device, such as a network device and/or a computing device, may be associated with that node. It is also noted that in the context of this patent application, the term "transmission" is intended as another term for a type of signal communication that may occur in any one of a variety of situations. Thus, it is not intended to imply a particular directionality of communication and/or a particular initiating end of a communication path for the "transmission" communication. For example, the mere use of the term in and of itself is not intended, in the context of the present patent application, to have particular implications with respect to the one or more signals being communicated, such as, for example, whether the signals are being communicated "to" a particular device, whether the signals are being communicated "from" a particular device, and/or regarding which end of a communication path may be initiating communication, such as, for example, in a "push type" of signal transfer or in a "pull type" of signal transfer. In the context of the present patent application, push and/or pull type signal transfers are distinguished by which end of a communications path initiates signal transfer.

Thus, a signal packet and/or frame may, as an example, be communicated via a communication channel and/or a communication path, such as comprising a portion of the Internet and/or the Web, from a site via an access node coupled to the Internet or vice-versa. Likewise, a signal packet and/or frame may be forwarded via network nodes to a target site coupled to a local network, for example. A signal packet and/or frame communicated via the Internet and/or the Web, for example, may be routed via a path, such as either being "pushed" or "pulled," comprising one or more gateways, servers, etc. that may, for example, route a signal packet and/or frame, such as, for example, substantially in accordance with a target and/or destination address and availability of a network path of network nodes to the target and/or destination address. Although the Internet and/or the Web comprise a network of interoperable networks, not all of those interoperable networks are necessarily available and/or accessible to the public.

In the context of the particular patent application, a network protocol, such as for communicating between devices of a network, may be characterized, at least in part, substantially in accordance with a layered description, such as the so-called Open Systems Interconnection (OSI) seven layer type of approach and/or description. A network computing and/or communications protocol (also referred to as a network protocol) refers to a set of signaling conventions, such as for communication transmissions, for example, as may take place between and/or among devices in a network. In the context of the present patent application, the term "between" and/or similar terms are understood to include "among" if appropriate for the particular usage and vice-versa. Likewise, in the context of the present patent application, the terms "compatible with," "comply with" and/or similar terms are understood to respectively include substantial compatibility and/or substantial compliance.

A network protocol, such as protocols characterized substantially in accordance with the aforementioned OSI description, has several layers. These layers are referred to as a network stack. Various types of communications (e.g., transmissions), such as network communications, may occur across various layers. A lowest level layer in a network stack, such as the so-called physical layer, may characterize how symbols (e.g., bits and/or bytes) are communicated as one or more signals (and/or signal samples) via a physical medium (e.g., twisted pair copper wire, coaxial cable, fiber optic cable, wireless air interface, combinations thereof, etc.). Progressing to higher-level layers in a network protocol stack, additional operations and/or features may be available via engaging in communications that are substantially compatible and/or substantially compliant with a particular network protocol at these higher-level layers. For example, higher-level layers of a network protocol may, for example, affect device permissions, user permissions, etc.

A network and/or sub-network, in an embodiment, may communicate via signal packets and/or signal frames, such as via participating digital devices and may be substantially compliant and/or substantially compatible with, but is not limited to, now known and/or to be developed, versions of any of the following network protocol stacks: ARCNET, AppleTalk, ATM, Bluetooth, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, and/or X.25. A network and/or sub-network may employ, for example, a version, now known and/or later to be developed, of the following: TCP/IP, UDP, DECnet, NetBEUI, IPX, AppleTalk and/or the like. Versions of the Internet Protocol (IP) may include IPv4, IPv6, and/or other later to be developed versions.

Regarding aspects related to a network, including a communications and/or computing network, a wireless network may couple devices, including client devices, with the network. A wireless network may employ stand-alone, ad-hoc networks, mesh networks, Wireless LAN (WLAN) networks, cellular networks, and/or the like. A wireless network may further include a system of terminals, gateways, routers, and/or the like coupled by wireless radio links, and/or the like, which may move freely, randomly and/or organize themselves arbitrarily, such that network topology may change, at times even rapidly. A wireless network may further employ a plurality of network access technologies, including a version of Long Term Evolution (LTE), WLAN, Wireless Router (WR) mesh, 2nd, 3rd, or 4th generation (2G, 3G, 4G, or 5G) cellular technology and/or the like, whether currently known and/or to be later developed. Network access technologies may enable wide area coverage for devices, such as computing devices and/or network devices, with varying degrees of mobility, for example.

A network may enable radio frequency and/or other wireless type communications via a wireless network access technology and/or air interface, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, ultra-wideband (UWB), 802.11b/g/n, and/or the like. A wireless network may include virtually any type of now known and/or to be developed wireless communication mechanism and/or wireless communications protocol by which signals may be communicated between devices, between networks, within a network, and/or the like, including the foregoing, of course.

Figure 4:
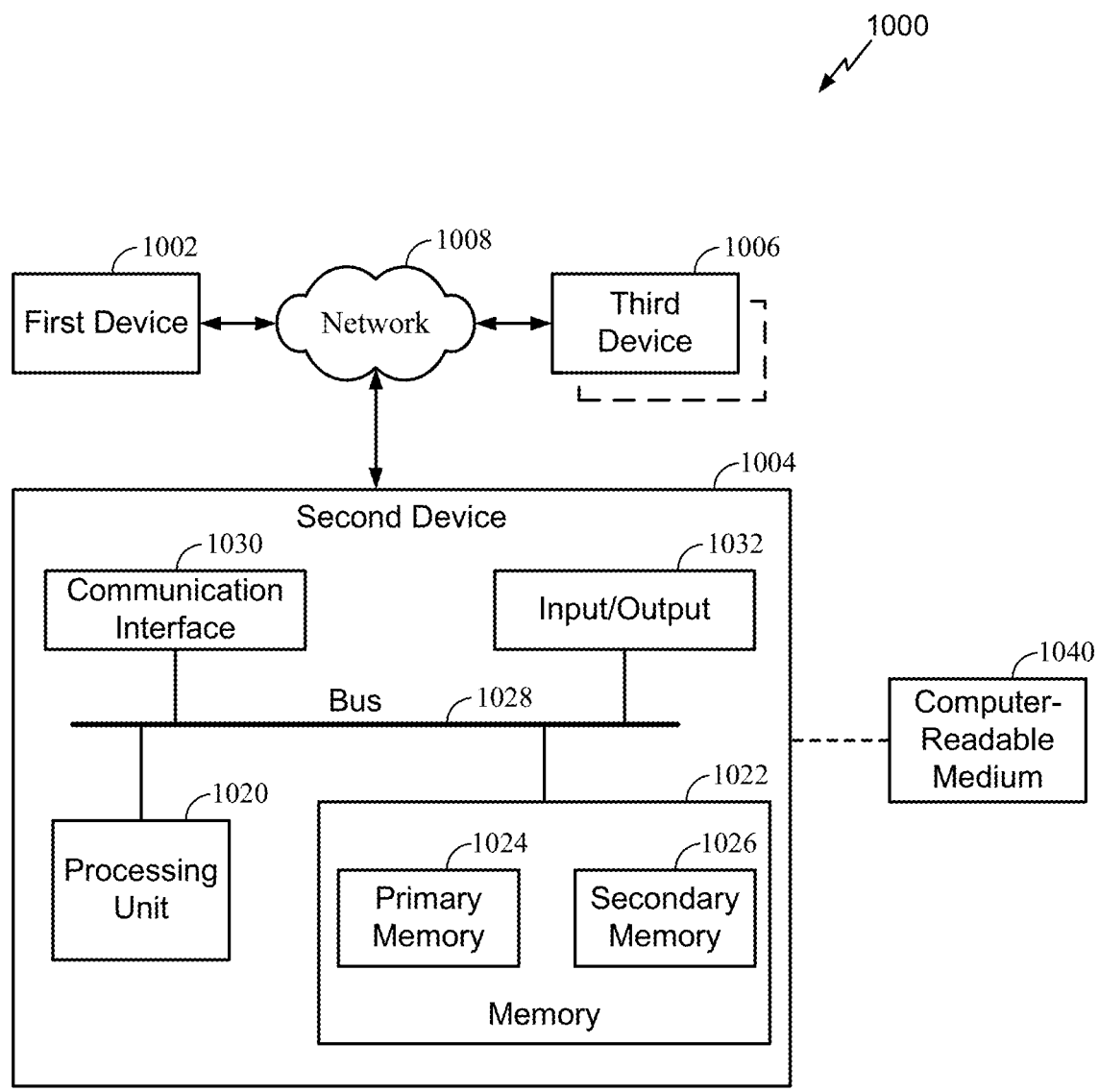
FIG. 4 is a schematic block diagram of an example computing system in accordance with an implementation.

In one example embodiment, as shown in FIG. 4, a system embodiment may comprise a local network (e.g., device 1004 and medium 1040) and/or another type of network, such as a computing and/or communications network. For purposes of illustration, therefore, FIG. 4 shows an embodiment 1000 of a system that may be employed to implement either type or both types of networks. Network 1008 may comprise one or more network connections, links, processes, services, applications, and/or resources to facilitate and/or support communications, such as an exchange of communication signals, for example, between a computing device, such as 1002, and another computing device, such as 1006, which may, for example, comprise one or more client computing devices and/or one or more server computing device. By way of example, but not limitation, network 1008 may comprise wireless and/or wired communication links, telephone and/or telecommunications systems, Wi-Fi networks, Wi-MAX networks, the Internet, a local area network (LAN), a wide area network (WAN), or any combinations thereof.

Example devices in FIG. 4 may comprise features, for example, of a client computing device and/or a server computing device, in an embodiment. It is further noted that the term computing device, in general, whether employed as a client and/or as a server, or otherwise, refers at least to a processor and a memory connected by a communication bus. A "processor," for example, is understood to connote a specific structure such as a central processing unit (CPU) of a computing device which may include a control unit and an execution unit. In an aspect, a processor may comprise a device that fetches, interprets and executes instructions to process input signals to provide output signals. As such, in the context of the present patent application at least, computing device and/or processor are understood to refer to sufficient structure within the meaning of 35 USC § 112 (f) so that it is specifically intended that 35 USC § 112 (f) not be implicated by use of the term "computing device," "processor" and/or similar terms; however, if it is determined, for some reason not immediately apparent, that the foregoing understanding cannot stand and that 35 USC § 112 (f), therefore, necessarily is implicated by the use of the term "computing device," "processor" and/or similar terms, then, it is intended, pursuant to that statutory section, that corresponding structure, material and/or acts for performing one or more functions be understood and be interpreted to be described at least in FIGS. 1-3 and in the text associated with the foregoing figure(s) of the present patent application.

Referring now to FIG. 4, in an embodiment, first and third devices 1002 and 1006 may be capable of rendering a graphical user interface (GUI) (e.g., including a pointer device) for a network device and/or a computing device, for example, so that a user-operator may engage in system use. Computing device 1004 may potentially serve a similar function in this illustration. Likewise, in FIG. 4, computing device 1002 ('first device' in figure) may interface with computing device 1004 ('second device' in figure), which may, for example, also comprise features of a client computing device and/or a server computing device, in an embodiment. Processor (e.g., processing device) 1020 and memory 1022, which may comprise primary memory 1024 and secondary memory 1026, may communicate by way of a communication bus 1015, for example. The term "computing device," in the context of the present patent application, refers to a system and/or a device, such as a computing apparatus, that includes a capability to process (e.g., perform computations) and/or store digital content, such as electronic files, electronic documents, measurements, text, images, video, audio, etc. in the form of signals and/or states. Thus, a computing device, in the context of the present patent application, may comprise hardware, software, firmware, or any combination thereof (other than software per se). Computing device 1004, as depicted in FIG. 4, is merely one example, and claimed subject matter is not limited in scope to this particular example.

For one or more embodiments, a device, such as a computing device and/or networking device, may comprise, for example, any of a wide range of digital electronic devices, including, but not limited to, desktop and/or notebook computers, high-definition televisions, digital versatile disc (DVD) and/or other optical disc players and/or recorders, game consoles, satellite television receivers, cellular telephones, tablet devices, wearable devices, personal digital assistants, mobile audio and/or video playback and/or recording devices, Internet of Things (IOT) type devices, or any combination of the foregoing. Further, unless specifically stated otherwise, a process as described, such as with reference to flow diagrams and/or otherwise, may also be executed and/or affected, in whole or in part, by a computing device and/or a network device. A device, such as a computing device and/or network device, may vary in terms of capabilities and/or features. Claimed subject matter is intended to cover a wide range of potential variations. For example, a device may include a numeric keypad and/or other display of limited functionality, such as a monochrome liquid crystal display (LCD) for displaying text, for example. In contrast, however, as another example, a web-enabled device may include a physical and/or a virtual keyboard, mass storage, one or more accelerometers, one or more gyroscopes, global positioning system (GPS) and/or other location-identifying type capability, and/or a display with a higher degree of functionality, such as a touch-sensitive color 2D or 3D display, for example.

As suggested previously, communications between a computing device and/or a network device and a wireless network may be in accordance with known and/or to be developed network protocols including, for example, global system for mobile communications (GSM), enhanced data rate for GSM evolution (EDGE), 802.11 b/g/n/h, etc., and/or worldwide interoperability for microwave access (WiMAX). A computing device and/or a networking device may also have a subscriber identity module (SIM) card, which, for example, may comprise a detachable or embedded smart card that is able to store subscription content of a user, and/or is also able to store a contact list. It is noted, however, that a SIM card may also be electronic, meaning that is may simply be stored in a particular location in memory of the computing and/or networking device. A user may own the computing device and/or network device or may otherwise be a user, such as a primary user, for example. A device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a computing and/or communications network may be embodied as a wired network, wireless network, or any combinations thereof.

A computing and/or network device may include and/or may execute a variety of now known and/or to be developed operating systems, derivatives and/or versions thereof, including computer operating systems, such as Windows, iOS, Linux, a mobile operating system, such as iOS, Android, Windows Mobile, and/or the like. A computing device and/or network device may include and/or may execute a variety of possible applications, such as a client software application enabling communication with other devices. For example, one or more messages (e.g., content) may be communicated, such as via one or more protocols, now known and/or later to be developed, suitable for communication of email, short message service (SMS), and/or multimedia message service (MMS), including via a network, such as a social network, formed at least in part by a portion of a computing and/or communications network, including, but not limited to, Facebook, LinkedIn, Twitter, and/or Flickr, to provide only a few examples. A computing and/or network device may also include executable computer instructions to process and/or communicate digital content, such as, for example, textual content, digital multimedia content, and/or the like. A computing and/or network device may also include executable computer instructions to perform a variety of possible tasks, such as browsing, searching, playing various forms of digital content, including locally stored and/or streamed video, and/or games such as, but not limited to, fantasy sports leagues. A computing and/or network device may also perform linguistic processing such as applying transforms to determine an embedding of tokens and/or apply attention models to determine service codes. The foregoing is provided merely to illustrate that claimed subject matter is intended to include a wide range of possible features and/or capabilities.

In FIG. 4, computing device 1002 may provide one or more sources of executable computer instructions in the form physical states and/or signals (e.g., stored in memory states), for example. Computing device 1002 may communicate with computing device 1004 by way of a network connection, such as via network 1008, for example. As previously mentioned, a connection, while physical, may not necessarily be tangible. Although computing device 1004 of FIG. 4 shows various tangible, physical components, claimed subject matter is not limited to a computing devices having only these tangible components as other implementations and/or embodiments may include alternative arrangements that may comprise additional tangible components or fewer tangible components, for example, that function differently while achieving similar results. Rather, examples are provided merely as illustrations. It is not intended that claimed subject matter be limited in scope to illustrative examples.

Memory 1022 may comprise any non-transitory storage mechanism. Memory 1022 may comprise, for example, primary memory 1024 and secondary memory 1026, additional memory circuits, mechanisms, or combinations thereof may be used. Memory 1022 may comprise, for example, random access memory, read only memory, etc., such as in the form of one or more storage devices and/or systems, such as, for example, a disk drive including an optical disc drive, a tape drive, a solid-state memory drive, etc., just to name a few examples.

Memory 1022 may be utilized to store a program of executable computer instructions. For example, processor 1020 may fetch executable instructions from memory and proceed to interpret and execute the fetched instructions. Memory 1022 may also comprise a memory controller for accessing device readable-medium 1040 that may carry and/or make accessible digital content, which may include code, and/or instructions, for example, executable by processor 1020 and/or some other device, such as a controller, as one example, capable of executing computer instructions, for example. Under direction of processor 1020, a non-transitory memory, such as memory cells storing physical states (e.g., memory states), comprising, for example, a program of executable computer instructions, may be executed by processor 1020 and able to generate signals to be communicated via a network, for example, as previously described. Generated signals may also be stored in memory, also previously suggested. In a particular implementation, processor 1020 may include general processing cores and/or specialized co-processing cores (e.g., signal processors, graphical processing unit (GPU) and/or neural network processing unit (NPU)), for example.

Memory 1022 may store electronic files and/or electronic documents, such as relating to one or more users, and may also comprise a computer-readable medium that may carry and/or make accessible content, including code and/or instructions, for example, executable by processor 1020 and/or some other device, such as a controller, as one example, capable of executing computer instructions, for example. As previously mentioned, the term electronic file and/or the term electronic document are used throughout this document to refer to a set of stored memory states and/or a set of physical signals associated in a manner so as to thereby form an electronic file and/or an electronic document. That is, it is not meant to implicitly reference a particular syntax, format and/or approach used, for example, with respect to a set of associated memory states and/or a set of associated physical signals. It is further noted an association of memory states, for example, may be in a logical sense and not necessarily in a tangible, physical sense. Thus, although signal and/or state components of an electronic file and/or electronic document, are to be associated logically, storage thereof, for example, may reside in one or more different places in a tangible, physical memory, in an embodiment.

Algorithmic descriptions and/or symbolic representations are examples of techniques used by those of ordinary skill in the signal processing and/or related arts to convey the substance of their work to others skilled in the art. An algorithm is, in the context of the present patent application, and generally, is considered to be a self-consistent sequence of operations and/or similar signal processing leading to a desired result. In the context of the present patent application, operations and/or processing involve physical manipulation of physical quantities. Typically, although not necessarily, such quantities may take the form of electrical and/or magnetic signals and/or states capable of being stored, transferred, combined, compared, processed and/or otherwise manipulated, for example, as electronic signals and/or states making up components of various forms of digital content, such as signal measurements, text, images, video, audio, etc.

It has proven convenient at times, principally for reasons of common usage, to refer to such physical signals and/or physical states as bits, service codes, tokens, computed likelihoods, values, elements, parameters, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically in the form of physical electronic and/or magnetic quantities, within memories, registers, and/or other storage devices, processing devices, and/or display devices of the special purpose computer and/or similar special purpose computing and/or network device. In the context of this particular patent application, as mentioned, the term "specific apparatus" therefore includes a general purpose computing and/or network device, such as a general purpose computer, once it is programmed to perform particular functions, such as pursuant to program software instructions.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation. Likewise, a physical change may comprise a transformation in molecular structure, such as from crystalline form to amorphous form or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state from a binary one to a binary zero or vice-versa in a memory device may comprise a transformation, such as a physical, but non-transitory, transformation. Rather, the foregoing is intended as illustrative examples.

Referring again to FIG. 4, processor 1020 may comprise one or more circuits, such as digital circuits, to perform at least a portion of a computing procedure and/or process. By way of example, but not limitation, processor 1020 may comprise one or more processors, such as controllers, microprocessors, microcontrollers, application specific integrated circuits, GPUs, NPUs, digital signal processors, programmable logic devices, field programmable gate arrays, the like, or any combination thereof. In various implementations and/or embodiments, processor 1020 may perform signal processing, typically substantially in accordance with fetched executable computer instructions, such as to manipulate signals and/or states, to construct signals and/or states, etc., with signals and/or states generated in such a manner to be communicated and/or stored in memory, for example.

FIG. 4 also illustrates device 1004 as including a component 1032 operable with input/output devices, for example, so that signals and/or states may be appropriately communicated between devices, such as device 1004 and an input device and/or device 1004 and an output device. A user may make use of an input device, such as a computer mouse, stylus, track ball, microphone, scanner, keyboard, and/or any other similar device capable of receiving user actions and/or motions as input signals. Likewise, for a device having speech to text capability, a user may speak to a device to generate input signals. A user may make use of an output device, such as a display, a printer, etc., and/or any other device capable of providing signals and/or generating stimuli for a user, such as visual stimuli, audio stimuli and/or other similar stimuli.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. A method comprising:
    determining an embedding of first tokens based, at least in part, on a linguistic analysis of an electronic document, the electronic document comprising one or more notes relating to a diagnosis and/or treatment created by a medical clinician, at least some of the first tokens to express elements of human anatomy, conditions of elements of human anatomy, or a combination thereof; and
    determining likelihoods of applicability of service codes, the service codes identifying clinical services to be performed for medical treatment on a patient, to the electronic document based, at least in part, on the embedding of tokens.

2. The method of claim 1, wherein determining the embedding of the first tokens further comprises:
    partitioning sentences expressed in the electronic document into components including words, partial words and/or punctuation; and
    associating the first tokens in a vocabulary of the first tokens with at least some of the components.

3. The method of claim 2, wherein:
    the embedding of first tokens comprises an array of context values associating the first tokens with the service codes identifying clinical services to be performed for medical treatment on the patient; and
    determining the embedding of the first tokens further comprises determining a linguistic context of at least some of the first tokens associated with the service codes.

4. The method of claim 3, wherein determining the linguistic context of at least some of the associated first tokens further comprises applying a bidirectional encoder representations from transformers (BERT).

5. The method of claim 4, and further comprising training the BERT using jargon, abbreviations, syntax, grammar and/or of text in a medical clinical service domain.

6. The method of claim 4, and further comprising applying the BERT according to a linguistic domain specific to a medical and/or clinical service.

7. The method of claim 1, wherein the embedding of first tokens comprises context values associated with individual tokens in a vocabulary of tokens and wherein determining the likelihoods of applicability of service codes to the electronic document further comprises:
    applying an attention model to the context values.

8. The method of claim 7, wherein applying the attention model to the context values further comprises, for computation of a likelihood of applicability of at least at least one of the service codes, computing a dot product of an array of attention coefficients and an array of at least some of the context values associated with the individual tokens.

9. The method of claim 1, wherein determining likelihoods of applicability service codes to the electronic document further comprises:
    applying a self-attention mapping to the embedding of the first tokens based, at least in part, on query, key and value components.

10. The method of claim 9, wherein determining likelihoods of applicability service codes to the electronic document further comprises:
    expressing interrelationships between and/or among code titles, the code titles to identify the service codes, in an embedding of second tokens; and
    applying an attention mapping to the embedding of first tokens, the attention mapping being based, at least in part, on the embedding of the second tokens.

11. A computing device comprising:
    one or more processors to:
    determine an embedding of tokens based, at least in part, on a linguistic analysis of an electronic document, the electronic document comprising one or more notes relating to a diagnosis and/or treatment created by a medical clinician, at least some of the tokens to express elements of human anatomy, conditions of elements of human anatomy, or a combination thereof; and
    determine likelihoods of applicability of service codes, the service codes identifying clinical services to be performed for medical treatment on a patient, to the electronic document based, at least in part, on the embedding of tokens.

12. The computing device of claim 11, wherein the one or more processors are further to:
    partition sentences expressed in the electronic document into components including words, partial words and/or punctuation; and
    associate tokens in a vocabulary of tokens with at least some of the components.

13. The computing device of claim 12, wherein the one or more processors are to determine the embedding of tokens based on a determination of a linguistic context of at least some of the associated tokens.

14. The computing device of claim 13, wherein determination of the linguistic context of at least some of the associated tokens further comprises application of a bidirectional encoder representations from transformers (BERT).

15. The computing device of claim 14, wherein the one or more processors are further to train the BERT using jargon, abbreviations, syntax, grammar and/or of text in a medical clinical service domain.

16. The computing device of claim 14, wherein the one or more processors are further to apply the BERT according to a linguistic domain specific to a medical and/or clinical service.

17. The computing device of claim 11, wherein the embedding of tokens comprises context values associated with individual tokens in a vocabulary of tokens and wherein determination of the likelihoods of applicability of the service codes to the electronic document further comprises:
    application of an attention model to the context values.

18. The computing device of claim 17, wherein application of the attention model to the context values further comprises, for computation of a likelihood of applicability of at least at least one of the service codes, computation of a dot product of an array of attention coefficients and an array of at least some of the context values associated with the individual tokens.

19. An article comprising:
   a non-transitory storage medium comprising computer-readable instructions stored thereon which are executable by one or more processors of a computing device to:
   determine an embedding of first tokens based, at least in part, on a linguistic analysis of an electronic document, the electronic document comprising one or more notes relating to a diagnosis and/or treatment created by a medical clinician, at least some of the first tokens to express elements of human anatomy, conditions of elements of human anatomy, or a combination thereof; and
   determine likelihoods of applicability of service codes, the service codes identifying clinical services to be performed for medical treatment on a patient, to the electronic document based, at least in part, on the embedding of tokens.

* * * * *